2 Sheets--Sheet 1.

C. WEST.

Piles-Supporters.

No. 5,839. Reissued April 14, 1874.

Attest,
F. W. Howard
Edwin James

Inventor,
Columbus West
per J. E. H. Holmead
Attorney.

2 Sheets--Sheet 2.

C. WEST.

Piles-Supporters.

No. 5,839. Reissued April 14, 1874.

Attest.
~~A. W. Howard~~
Edwin James.

Inventor.
Columbus West
per J. E. H. Holmead
Attorney.

UNITED STATES PATENT OFFICE.

COLUMBUS WEST, OF PITTSBURG, PENNSYLVANIA.

IMPROVEMENT IN PILES-SUPPORTERS.

Specification forming part of Letters Patent No. 142,972, dated September 16, 1873; reissue No. 5,839, dated April 14, 1874; application filed March 13, 1874.

*To all whom it may concern:*

Be it known that I, COLUMBUS WEST, of Pittsburg, in the county of Allegheny and State of Pennsylvania, have invented certain Improvements in Piles-Supporters, on which Letters Patent of the United States were granted bearing date September 16, 1873, and numbered 142,972; that the following is a full, clear, and exact description of said invention, reference being had to the accompanying drawing and the letters of reference marked thereon, making part of this specification, in which—

Figure 1:
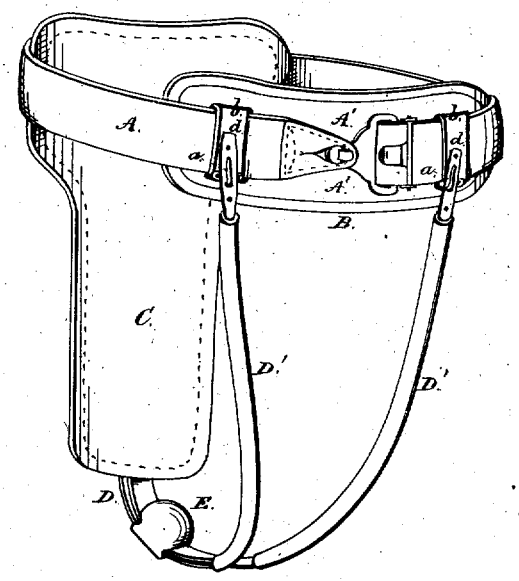
Figure 2:
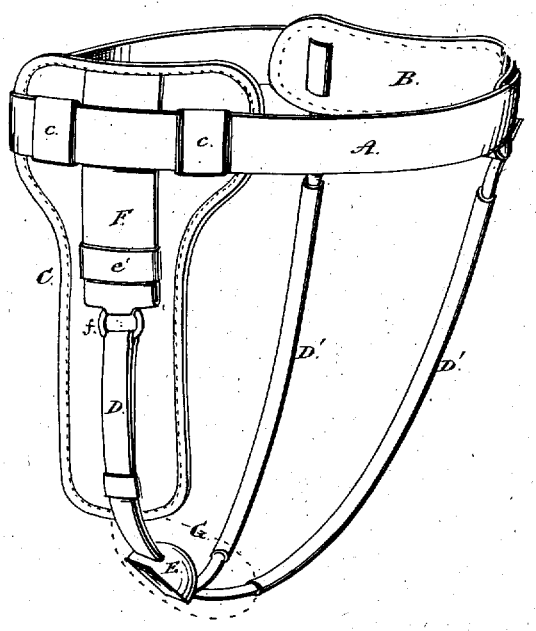
Figure 3:
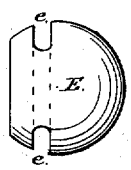
Figure 4:
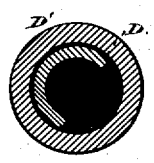

Figure 1 is a front view in perspective. Fig. 2 is a rear view in perspective. Fig. 3 is a side view of the ball. Fig. 4 is a vertical sectional view of one of the front straps.

The object of my improvement is to provide a cheap, simple, and practical support to be used for the relief and cure of prolapsus ani or protruding bowels and external hemorrhoids or piles. I so protect the person of the wearer from direct contact with the straps that support the pad as to avoid all cutting or chafing of the flesh. My invention relates chiefly to a novel arrangement of the supporting-straps for the anus-pad and their attachments. The front straps, or the straps that pass up over the stomach of the patient, are non-elastic, and are inclosed in a small rubber tube, which not only renders them comfortable to wear, but prevents their chafing. These front straps are connected with the waistband or belt by means of hooks and eyes, and in such manner as to be detachable at pleasure. The rear straps, instead of being attached directly to the waistband, are secured thereto by means of a back piece or brace-pad, which, when the truss is being worn, projects downward sufficiently far to protect the body of the wearer from all direct contact with said rear straps, and which is of the greatest importance, especially as these straps are elastic, and consequently are always taut or held with a tight and binding pressure, and which would necessarily irritate and chafe the patient were it not for the protection which the pad affords; and the pressure incident to the extending or contracting of the straps is also borne directly by this pad, and without the slightest inconvenience to the wearer; and, besides, this pad acts as a positive brace, strengthening the parts where there is the greatest weakness. My invention also consists in using, in connection with the rear brace-pad and the hook-and-eye attachment, an adjustable anus-pad constructed of a solid ball of rubber. The shape of this pad corresponds to the form of the anus, and is of such dimensions as to allow of its projecting or, when a sponge is used, of its pressing the sponge into the anus sufficiently far to close and support it. This pad is formed with a slot at its base, and is slipped over the supporting-straps, and, owing to the fact of its sliding freely thereon, may be adjusted at pleasure.

The construction and operation of my invention are as follows:

A is the waistband or belt, which is constructed of any suitable material, and is fastened by means of a buckle, A′. To this belt A are secured two pads, one, B, being in front, and the other, C, at the rear. This pad C is of a peculiar form, and is of such dimensions as to furnish a broad bearing at its upper section so as to prevent the waistband from cutting or chafing the wearer; and, also, is to be of such form and dimensions as to extend down such a distance as to render it impossible for the bearing-straps to be brought in contact with the crotch, immediately below the spinal column, and consequently avoiding chafing at this point, and at the same time securing perfect adjustability; and as the elastic material to which the bearing-straps are secured exerts its expansive and contractile force on the outer surface of this pad C it is impossible, no matter what position the body may be caused to assume, that the straps should be so drawn or extended as to be uncomfortable. This belt A passes through loops *b b* and *c c* on the outer faces of these pads, and by means of which they are relatively held in their desired positions. These pads are of the form shown in the accompanying drawing, and are constructed of leather or of some other suitable material which possesses the desired stiffness. D is the supporting-strap of the anus-pad E, and is constructed of leather or other suitable material. This strap is looped into a ring, *f*, which is secured at the end of a heavy piece of elastic webbing, F, and which is sewed to the upper section of the pad C, as clearly shown in Fig. 2. This piece F passes under the belt A, by means of which, and the loop $e'$, it is secured and held in proper position on the pad C. This strap D having been looped so as to secure the desired bearing in the ring $f$, its free ends are passed through short sections D′ D′ of rubber tubing, and are fastened to the front pad B by means of the hooks $a$ $a$, as clearly shown in Fig. 1. E is the anus-pad, and is substantially of the form shown in Fig. 3. Through the base of the pad is cut or mortised a slot, $e$, through which passes the straps D D. This anus-pad E slides freely over the straps, which permits of its being adjusted, and its relative position in connection with the straps changed or arranged at pleasure. At G, dotted lines, Fig. 2, is shown a sponge or sponges, which I propose to use in connection with my improvement, or, if desired, two sponges may be used. Especially is this desirable in case the patient should desire to use any piles ointment. On preparing the sponges for use in connection with my improvement, I trim or thin them at such sections as are to fit over or around the anus-pad, and which causes them in use so much the more readily to conform to the contour of the anus-pad.

From the foregoing description the operation of my improvement will readily be understood. The straps D D, having been unhooked, are left free. The parts having been bathed with a sponge, and the water squeezed out of the same, it is ready, if desired, to be used in connection with my improvement. The pad E is now slipped along the strap D to the desired point, or to such position as will afford the proper and most direct support for the same. The sponge is now placed over the pad E, and if ointment is used a small sponge is placed over that. The straps are now passed up over the front of the body or stomach, extending up in an angular position, and are fastened by the hooks $a$ $a$ in either of the series of openings $d$ $d$.

And now the great advantages of my improvement will be readily understood. Instead of the front straps cutting and chafing, the patient has only in contact with this portion of his body the round, soft, and yielding surface of the rubber tubes, and which always retain their shape and are pleasant and comfortable to wear. The pad C, at the rear of the patient and under his seat, holds the straps entirely free from all direct contact. The pad extending, as it does, down to a point below the line of the anus, its lower end acts as a ridge to hold the straps away, and consequently, no matter how great the inflammation and irritation immediately around these parts may be, the straps can in no manner chafe or rub, while, with the pad extending down as it does, it acts as a protector, so as to strengthen the parts, the strap F causing the truss readily to yield to each and every motion of the body.

One of the greatest conveniences that will be experienced in connection with this truss is the readiness with which the patient is enabled to use the stool. He simply has to unhook the hooks $a$ $a$ and remove the sponges, and swing the straps and pad back, passing the straps over and tucking them under the waistband. This is a feature of great practical utility, and obviates the necessity and inconvenience of frequently removing and replacing the whole support.

What I claim as new, and desire to secure by Letters Patent of the United States, is—

1. The supporting-straps D D and rubber tubes D′ D′, when the same are so combined and arranged as to operate substantially as described, as and for the purpose specified.

2. The pad C, to serve as a rear support for the attaching-straps of an anus-pad, of the form shown, constructed in a manner to act substantially as described.

3. The brace-pad C, sliding rubber anus-pad E, and double supporting-straps D and their tubes D¹, the whole being combined and arranged to operate substantially as described.

In testimony whereof I have signed my name to this specification before two subscribing witnesses.

Witnesses: COLUMBUS WEST.

EDWIN JAMES,

JOS. T. K. PLANT.